United States Patent
Van Den Braak et al.

(10) Patent No.: US 6,509,044 B2
(45) Date of Patent: *Jan. 21, 2003

(54) STABLE, OPTICALLY CLEAR COMPOSITIONS

(75) Inventors: Maarten Van Den Braak, Coleford (GB); Andrew Symonds, Bream (GB); Michael Anthony Ford, Coleford (GB)

(73) Assignee: SmithKline Beecham p.l.c. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/825,433

(22) Filed: Apr. 2, 2001

(65) Prior Publication Data

US 2001/0026805 A1 Oct. 4, 2001

Related U.S. Application Data

(63) Continuation of application No. 09/043,373, filed as application No. PCT/EP96/04168 on Sep. 19, 1996, now Pat. No. 6,251,441.

(30) Foreign Application Priority Data

Sep. 23, 1995 (GB) ............................................. 95 19468

(51) Int. Cl.$^7$ ............................................... A23L 1/275
(52) U.S. Cl. ........................... 426/2; 426/262; 426/544; 426/602
(58) Field of Search .............................. 426/2, 262, 541, 426/542, 544, 602, 654, 417

(56) References Cited

U.S. PATENT DOCUMENTS

| 3,886,294 A | 5/1975 | Emodi et al. ................ 426/540 |
| 4,835,002 A | 5/1989 | Wolf et al. .................. 426/590 |

FOREIGN PATENT DOCUMENTS

| EP | 0 571 677 | 1/1993 |
| EP | 0 659 347 | 6/1995 |
| WO | WO 94/06310 | 3/1994 |
| WO | WO 95/24832 | 9/1995 |

OTHER PUBLICATIONS

Microemulsions—Theory and Practice, Academic Press, Inc., pp. 33–55, Leon M. Price editor, Jan. 1977.

*Primary Examiner*—Keith Hendricks
(74) *Attorney, Agent, or Firm*—Dara L. Dinner; Theodore R. Furman; Charles M. Kinzig (57) ABSTRACT

A process for preparing an aqueous composition for the preparation of optically clear products, especially beverages, having enhanced stability in syrup and bioavailability for human or animal healthcare. The compositions include an oil soluble ingredient and a primary and a secondary surfactant which match the fatty acid profile of the oil soluble ingredient and follow specific ratios of oil soluble ingredient to emulsifier and specific ratios of primary to cosurfactant.

19 Claims, 5 Drawing Sheets

STABLE, OPTICALLY CLEAR COMPOSITIONS

This is a continuing application of U.S. Ser. No. 09/043,373, filed Aug. 7, 1998, now U.S. Pat. No. 6,251,441, and which is the §371 national stage entry of PCT/EP96/04168, filed Sep. 19, 1996.

The present invention relates to a process for preparing compositions comprising oil soluble ingredients for use in the maintenance and/or promotion of health. In particular the invention relates to compositions for products for internal or external use by humans or animals such as beverages and capsules, processes for preparing such compositions and products containing them.

WO/94/06310 discloses an aqueous composition for the preparation of optically clear products for use in human and animal healthcare comprising 0.1 to 2.0% of an oil soluble ingredient as a 20–30% dispersion in a suitable oil or 0.1 to 5.0% w/v as the pure crystalline compound 2–20% of an emulsifier mixture having an HLB value of between 10 and 18 or where a blend of emulsifiers is employed, a calculated HLB value of between 10 and 18 and 0.1% of an antioxidant or a mixture of antioxidants.

In "Microemulsions Theory and Practice" (Edited Leon M Prince chapter 3, Academic Press Inc, NY, 1977) it is stated that stable microemulsions result when an emulsifier is chosen that is chemically matched to the oil. Also in order to form satisfactory emulsions it can be helpful to use two kinds of emulsifier, a primary surfactant and a cosurfactant.

However, a problem encountered with existing compositions has been the stability of emulsions in the presence of certain carbohydrates (particularly syrups) especially those containing polymerised molecules. A particular problem is the formation of occlusion compounds or complexes on long term (several months) storage.

We have now found that a composition having enhanced bioavailability and stability in syrup can be obtained by using an emulsifier mixture comprising fatty acid residues which chemically matches the fatty acid residues of the oil soluble ingredient or a dispersion of the oil souluble ingredient and using specific ratios of oil or oil dispersion to emulsifier and specific ratios of primary to cosurfactant.

Accordingly, the present invention provides a process for preparing an aqueous composition for the preparation of optically clear products having enhanced stability in syrup and bioavailability for human or animal healthcare comprising a) mixing 0.001–2.0% of an oil soluble ingredient or 0.1–2.0% w/w of an oil soluble ingredient as a 20–30% dispersion in a suitable oil with 2–10% of an emulsifier mixture having an HLB (hydrophilic lipophilic balance) value of between 10 and 18 and heating to between 25 and 150° C. so as to yield a transparent mixture b) combining the mixture with water while continuously stirring to provide a transparent composition characterised in that the emulsifier mixture is a combination of a primary surfactant and a secondary or cosurfactant, wherein the fatty acid profile of the emulsifier mixture matches the fatty acid profile of the oil soluble ingredient or the dispersion of an oil soluble ingredient, the HLB of the primary surfactant is greater than the cosurfactant and the weight ratio of oil or oil dispersion to emulsifier is between 1:1 and 1:7 and the ratio of primary to cosurfactant is between 10:1 and 200:1.

Preferably the ratio of oil or oil dispersion to emulsifier is between 1:1 and 1:5. Preferably the ratio primary to cosurfactant is between 20:1 and 50:1, and is most suitably about 30:1.

Surprisingly, in addition to solving the problem of the formation of occlusion complexes, it has been found that by including a small amount of a cosurfactant allows less overall emulsifier is used. This is particularly valuable in the case of syrup containing beverages where reducing emulsifier content has cost and taste benefits and reduces the amounts of 'synthetic' components.

The present invention allows the formation of stable compositions in syrups which are typically up to 60 Brix, using very low amounts of emulsifier. This is particularly useful in the formulation of products especially energy drinks and capsules where excess amounts of emulsifiers along with carbohydrates can lead to the formation of occlusion products during long term (several months) storage.

An important advantage of the compositions of the present invention over known compositions is one of economy since it allows products with minimal amounts of emulsifiers to be developed. The compositions are particularly useful for incorporation of biologically active oils into aqueous preparations in a microdispersed form that facilitates uptake.

Preferably the mixture in a) is added to the water. Preferably one or more antioxidant(s) is first dispersed with the emulsifiers in a). Suitably the oil soluble ingredient is a biologically active oil by which we mean natural or synthetic oils which are or contain biologically active agents in particular prophylactic or therapeutic agents.

The composition of the present invention is able to yield a product with desirable properties, particularly high water solubility, using ingredients which have hitherto been found to be difficult to solubilise satisfactorily in this kind of product.

Preferably the biologically active oil is an oil of natural origin for example from the seeds or flowers of the Ribes. Boraginaceae, Labiataea, Onagraceae and Curcubitaceae species, oils of fungal origin, fish oils or other natural oils. Preferred oils include evening primrose oil, borage/starflower oil and blackcurrant seed oil. Preferably the oil soluble ingredient comprises a colouring ingredient.

Compositions containing β carotene as an oil soluble ingredient have been particularly successful. Particularly suitable sources of β carotene include both natural and synthetic β carotene as dispersions in oil (as available from various commercial sources including those mentioned herein).

Suitably the amount of oil is 0.001–2.0%, preferably 0.1–1.0% by weight expressed as the pure substance. Oils for use in the present invention can be extracted from natural sources by processes known in the art. The oils are commercially available, for example, from Sigma Chemical Co., Poole, Dorset. The compositions can contain more than one biologically active oil.

Other biologically active ingredients can be used in the composition according to the invention, in particular carotenoid pigments eg. β carotene to produce a useful combination of colour and nutritional biochemicals.

The biologically active oils may be mixed or dispersed with other suitable oils in particular, consumable oils for example, corn, peanut, safflower, olive and rapeseed oils as well as many essential oils particularly those used in beverages used to give flavours, such as citrus oils.

The emulsifiers may be any anionic, cationic, amphoteric or non-ionic emulsifier which are suitable for consumption by or application to the human or animal body. Preferably the emulsifiers are non-ionic emulsifiers having an HLB (hydrophilic/lipophilic balance) of 12–16 and most preferably has an HLB value of 15. Preferred mixtures include Tween 80 (polyoxyethylenesorbitan monooleate) and Span 80 (sorbitan monooleate) available from ICI Speciality Chemicals, Leatherhead, Surrey or from Sigma Chemical Company, Poole, Dorset.

Suitably the emulsifier mixture is a binary or tertiary blend of emulsifiers, for example blends of Tween 60 with a sucrose ester emulsifier (manufactured by Mitsubishi Kasei Food Corporation, Ichikawa Building, 13-3 Ginza 5-Chome, Chuo-ku, Tokyo 104, Japan) or blends of Tween 60 and sucrose ester and a polyglycerol ester of a fatty acid (available from Grindsted Products Limited., Northern Way, Bury St. Edmunds, Suffolk).

The amount of emulsifier mixture in the composition is selected as an amount which will vary depending upon which specific biologically active oil is used, its method of preparation, and how much is included. For example an oil-based dispersion containing 1% by weight of biologically active oil will generally require an emulsifier mixture in the range of 1–8-% w/w to achieve a clear dispersion and so as not to have significant adverse flavour effects in typical products when diluted.

Preferably the emulsifier mixture comprises a polysorbate, in particular polysorbate 60 in the case of consumable products as it has the advantage of having the least noticeable taste. Therefore, a particularly useful feature of the present invention is the ability to produce a flavourless composition.

The composition advantageously comprises in addition an antioxidant which can be for example, alpha-tocopherol, tocopheryl acetate, ascorbic acid, ascorbyl palmitate, butylated hydroxyanisole (BHA) and butylated hydroxytoluene (BHT) or a mixture of such antioxidants. Particularly preferred antioxidants are α-tocopherol, tocopheryl acetate, ascorbyl palmitate and ascorbic acid.

Whilst the present invention is particularly useful in the production of optically clear products, the present invention can also be used to prepare opaque, cloudy products. A frequent problem with such products, particularly those products containing emulsified oils is that of 'neck ringing'. The compositions prepared according to the present invention have been found not to exhibit this problem. It will be appreciated that the compositions of the present invention may be used for products in the pharmaceutical or veterinary field other than beverages, such as vitamin and cough syrups, throat sprays, lotions and mouthwashes, particularly where optical clarity is important.

Certain biologically active oils contain vitamins and pro-vitamins such as vitamins A, D, E, carotenoid pigments and nutritionally important fatty acids.

In the compositions of the present invention the biologically active oils are believed to be finely dispersed in a micellar form or as microemulsions because they exhibit certain characteristics eg. transparency when viewed by transmitted light. Therefore a further advantage of the compositions according to the present invention is that the fine dispersion of these oils in aqueous preparations will help to promote their efficient uptake by body tissues when the composition is presented to the body. Whilst the small particle size of the particles of biologically active oils favour their uptake, the simultaneous presentation or ingestion of the oils with an emulsifier will also encourage efficient transfer of these substances across membranes.

The formulations according to the invention also have acid resistance. This is advantageous because prior to absorption from the intestinal tract, the preparation is able to survive the strongly acid conditions of the stomach.

In a further aspect of the invention there is provided a method of administration of an oil-soluble material to human or animal body by treating said body with a composition according to the invention. Preferably the composition is administered orally, for example in the form of a liquid composition.

The composition obtained according to the present invention is an aqueous dispersion which is capable of dissolution in water-based products to yield optically clear finished products. It will be appreciated that further ingredients may optionally be included in the composition of the present invention or to the final food product, for example sweeteners, preservatives (eg. sulphur dioxide, benzoic acid and sorbic acid), proteins, fats, vitamins, minerals and other materials employed in the preparation of food and drink products. Optionally the compositions also contain antioxidant cofactors such as zinc, selenium and manganese which are needed for the body's naturally occurring antioxidant enzymes. Preferably the final product is flavoured; this can be achieved by the addition of naturally flavoured foods such as fruit juices and concentrates, extracts and compounds or flavouring additives. Preferably further nutritive ingredients are added to the final drink such as other vitamins and minerals as described in "The Food Labelling Regulations 1984" Statutory Instrument No. 1305 (1984) H.M.S.O., London.

Suitably processing aids can be incorporated. Such aids may include ingredients which influence pH, redox potential, enzyme activity, hydrogen bonding and/or other aspects. Processing aids are for example sulphur dioxide, other antioxidants, metal salts, acids (eg. phosphoric and citric acid), alkalis, surfactants such as lecithin and starch plasticisers eg. calcium chloride. Preferred processing aids for inclusion are anti-foaming agents eg. silicones.

Ingredients subject to a loss of nutritional value are added at a late stage of the process. Optionally the product can be produced in light or oxygen excluding containers after preparation to increase protection of materials sensitive to light or oxygen induced degradation. Optionally the product can be carbonated.

The use of these high temperatures incurs the risk of degradation of the oil unless suitable precautions are taken. For example it is desirable to exclude oxygen by heating the mixture in an atmosphere of nitrogen. In a further aspect of the present invention additional water is added to the composition to yield an aqueous intermediate product which is suitable for use in a suitable water-based product.

In a further aspect of the invention there is provided the use of carotene microemulsions to deliver high bioavailability carotenes to the blood and to tissues for use in medicine. The invention is illustrated by the following Examples.

EXAMPLES

Experiments were carried out to develope compositions with maximum stability and clarity in syrup. Primary surfactants of high HLB values were selected so as to chemically match as far as possible the oil present in the composition. For example, in the following compositions where β-carotene (30% dispersion) is dispersed in a vegetable oil rich in oleic acid, emulsifiers rich in oleic acid residues were used. The chosen primary surfactants were initially screened by preparing microemulsions which comprised a large excess of emulsifiers. While some microemulsions were opaque others were transparent. Using the primary surfactants producing transparent microemulsions, a number of co-surfactants were selected. These were of lower HLB values but similar in chemical composition to the respective primary surfactants. It was found that the inclusion of a small amount of particular cosurfactants enabled the amount of total emulsifier to be reduced and resulted in improved stability of the microemulsion.

The ratio of primary surfactant to cosurfactant was determined by preparing a series of phase diagrams that graphically represent how the composition is related to the transparency of the micremulsion, so as to provide enough information to optimise the composition further. Further experiments were then designed to optimise the microemulsions. A statistical approach [e.g Box, G. E. P., Hunter, W. G. and Hunter, J. S. (1978) Statistics for Experimenters] allowed a reduction in the total number of experiments required. The results generated were plotted out using "Minitabs for Windows" statistics software (Version 10, Minitab Inc., State College, Pa. USA).

The clarity of each microemulsion was determined by measuring the transmission of light at 800 nm through each microemulsion. A polynomial equation was generated that could then be used to explain the relationship between the composition of the microemulsions and their clarity. This equation was used to generate the contour and response surface plots shown in FIGS. 1 and 2. To determine the optimum composition for optimum stability in syrup a similar approach was used, but after preparation of each microemulsion a small proportion was added to syrup, heated to 70 degrees C., cooled and the clarity determined. A polynomial equation was generated to explain the relationship between microemulsion composition and clarity. This was used to generate the contour and response plots of microemulsion clarity after one hour in syrup. As can be seen from comparing plots in FIGS. 3 and 4 with those in FIGS. 1 and 2 the compositions which afford optimum clarity after heating in syrup is not the same as those in the absence of syrup.

Example 1.1

Composition

|  | % w/w |
| --- | --- |
| β-carotene * (30% dispersion) | 0.3 |
| emulsifier (polysorbate 80) | 3.5 |
| emulsifier (sorbitan monooleate) | 0.7 |
| water to | 100 |

* From F. Hoffman-La Roche, Basel, Switzerland. Tradename β carotene 30% FS.

The β-carotene is dispersed in the two emulsifiers and the mixture is heated to 140° C. with stirring. At this point the mixture should remain transparent. Finally, the mixture is combined with hot water and then cooled rapidly.

Figure 1:
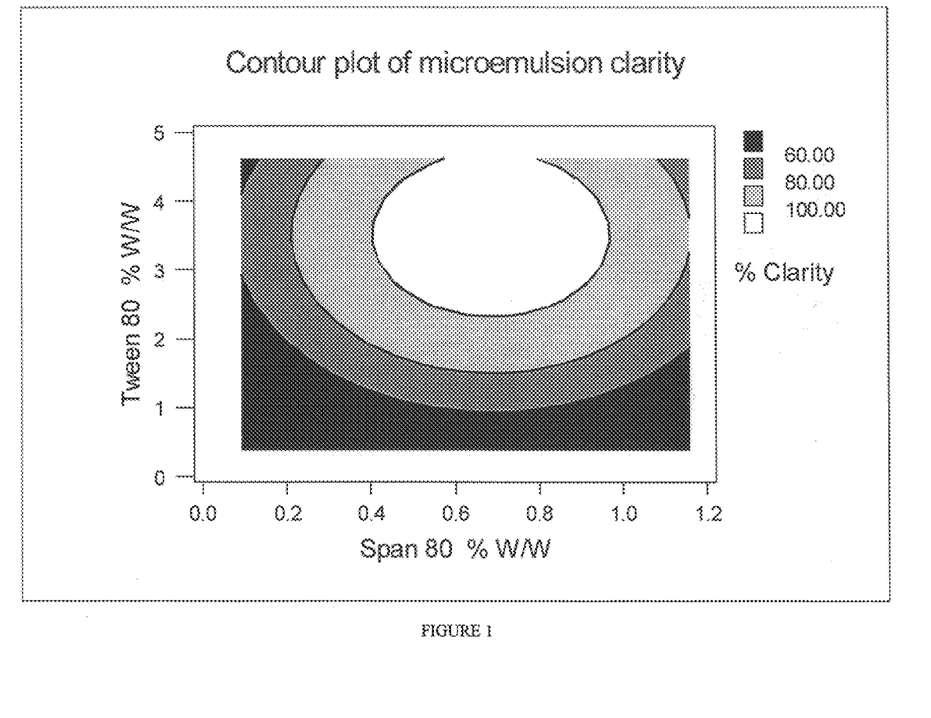
FIG. 1: Contour plot of microemulsion clarity.
Figure 2:
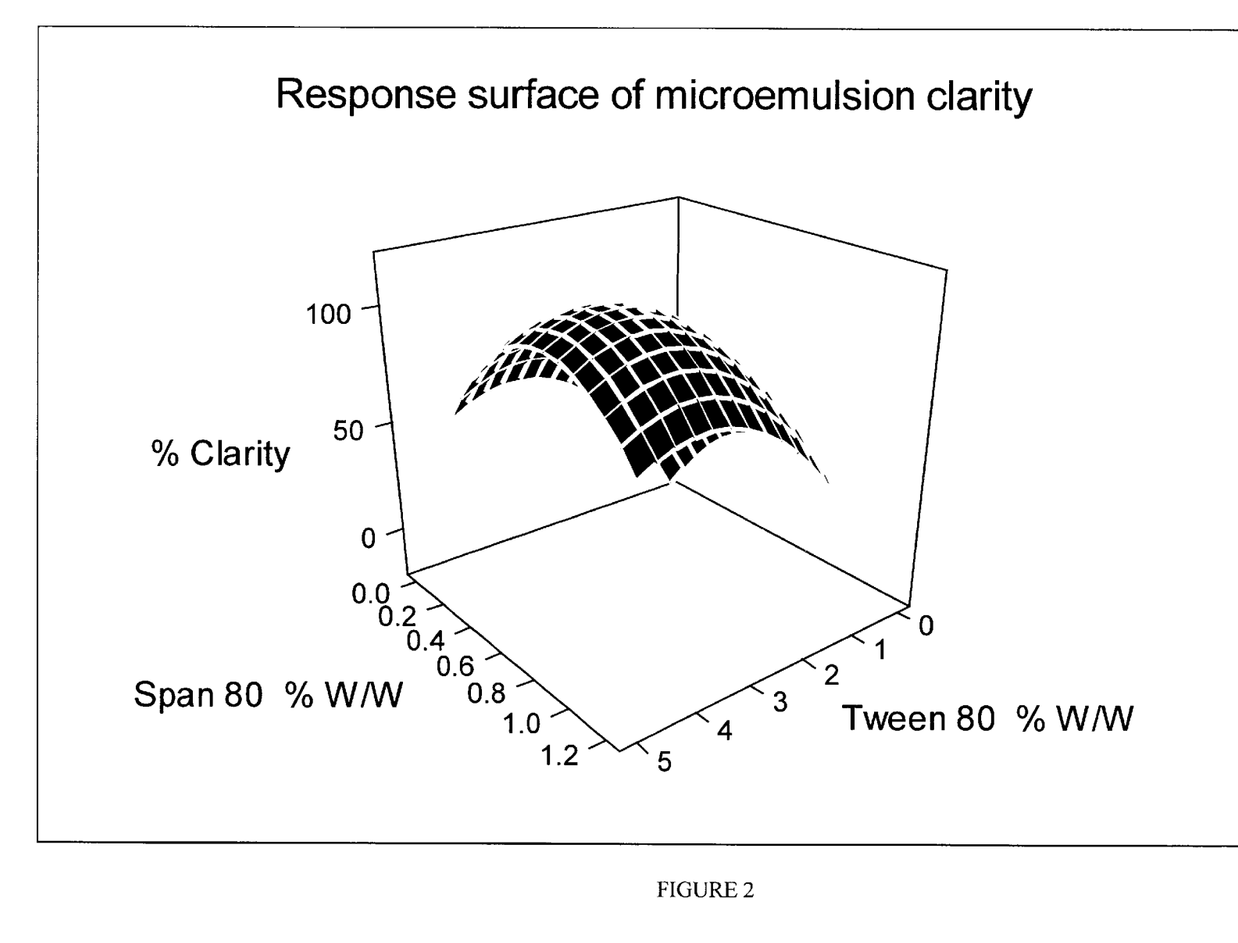
FIG. 2: Response surface of microemulsion clarity.

The contour and response surface plots in FIGS. 1 and 2 show the compositions of polysorbate 80 and sorbitan mono oleate that are needed to produce microemulsions with maximum clarity.

The emulsifier mixture satisifies the formula:

% Transmission=−59.4+63.8 (Tween 80 g/100 g0)+169 (Span 80 g/100 g)−9.16 (Tween 80 g/100 g)$^2$−119 (Span 80 g/100 g)$^2$ Example 1.2

Colour Composition for Maximum Stability in Syrup

|  | % w/w |
| --- | --- |
| β-carotene * (30% dispersion) | 0.33 |
| emulsifier (polysorbate 80) | 5 |
| emulsifier (sorbitan monooleate) | 0.15 |
| water to | 100 |

* See example 1.1

The β-carotene is dispersed in the two emulsifiers and the mixture is heated to 140° C. with stirring. At this point the mixture should remain transparent. Finally, the mixture is combined with hot water as detailed in Example 1.1. These compositions have been stable for 1 year.

Figure 3:
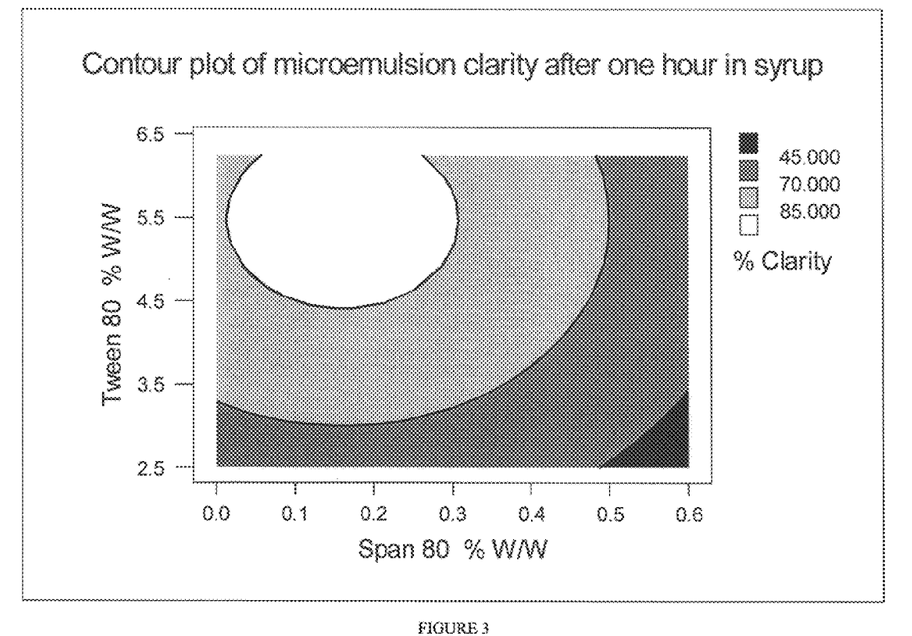
FIG. 3: Contour plot of microemulsion clarity after one hour in syrup.
Figure 4:
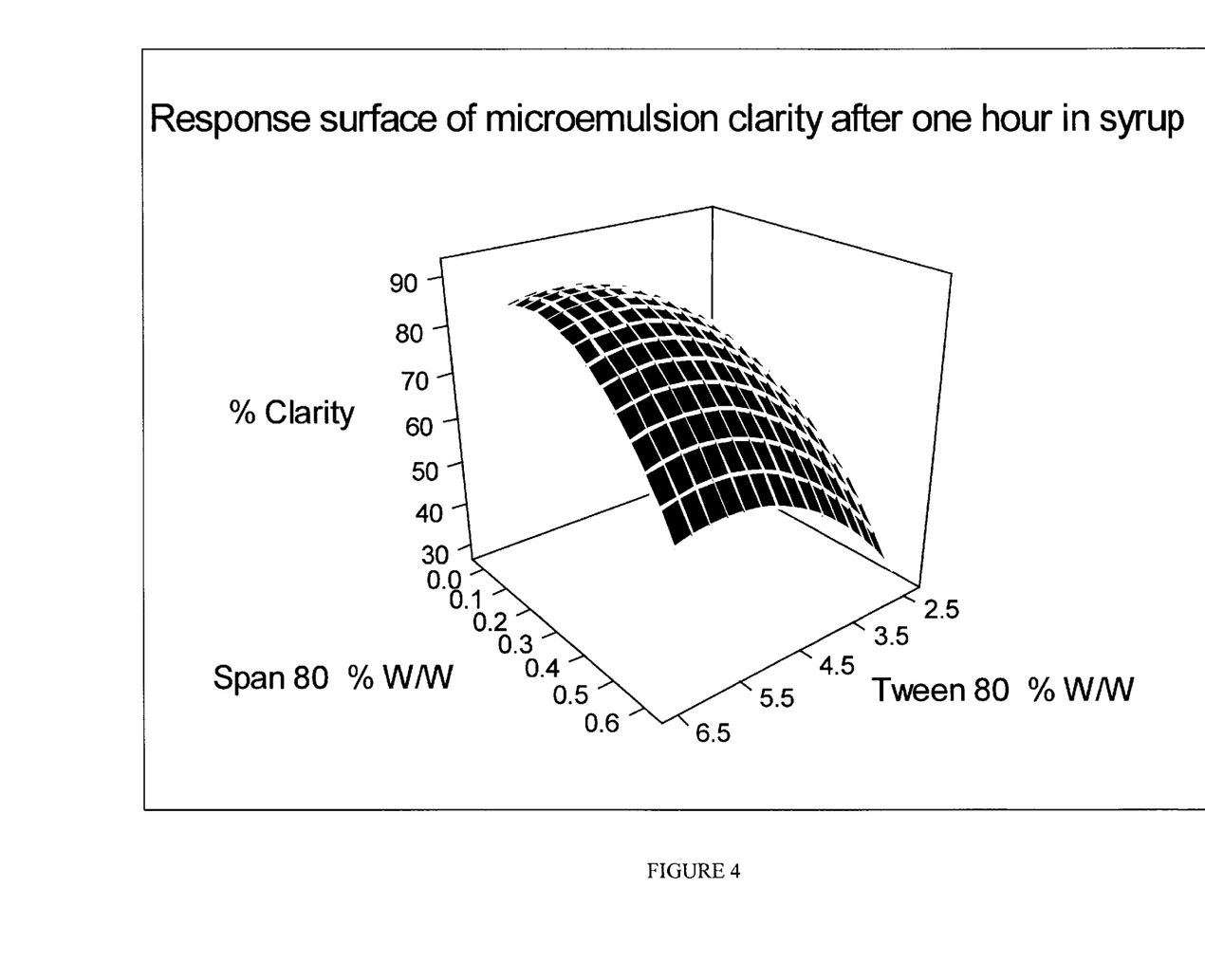
FIG. 4: Response surface of microemulsion clarity after one hour in syrup.

The contour and response surface plots in FIGS. 3 and 4 show the compositions of polysorbate 80 and sorbitan mono oleate required to produce microemulsions with maximum stability when added to a syrup concentrate.

The resulting clarity is defined by the equation:

% transmission=−5.2+32.5 (Tween 80% W/W)+51 (Span 80% W/W)−3 (Tween 80% W/W)$^2$−159 (Span 80% W/W)$^2$ Example 1.3

β-Carotene Composition Used in Bioavailability Study (Example 2)

|  | % w/w |
| --- | --- |
| β-carotene *(30% dispersion) | 0.45 |
| emulsifier (polysorbate 60) | 6 |
| emulsifier (sucrose stearate) | 0.7 |
| water to | 100 |

* See example 1.1

The β-carotene is dispersed in the polysorbate 60 and the mixture is heated to 140° C. with stirring. The sucrose stearate is added with continued stiring until the mixture is transparent. The mixture is then added to hot water as detailed in example 1.1.

Example 1.4

Manufacture of Flavoured Concentrate for Bottling

A flavoured concentrate is prepared by mixing the following ingredients together with stiring. The flavourings and microemulsion composition are added last.

|  | % w/w |
| --- | --- |
| Glucose syrup (S.G 1.4) | 63.27 |
| Preservatives | 0.07 |
| Acidulants | 0.89 |
| flavourings | 0.03 |
| water | 35.45 |
| β-carotene microemulsion composition | 0.28 |
| Total | 100.00 |

The quality criteria are;

| Refractometric soluble solids, | °Brix of 50.8 ± 0.5 |
| --- | --- |
| Acidity, expressed as citric acid % w/w | 0.76 ± 0.04 |

The flavoured concentrate is pasteurised at 91° C.±2° C. for 42±3 seconds and cooled to below 30° C. One part flavoured concentrate is diluted with 2.25 parts water prior to bottling. In this example the microemulsion composition contains 0.45% w/v β-carotene and the finished product contains 4.5 mg β-carotene per litre.

The concentration of biologically active oil in the finished product can be changed by varying the microemulsion composition and/or by varying the amount of microemulsion composition that is added to the flavoured concentrate.

Example 2

Bioavailability Study

A comparison was made of the bioavailability, in healthy volunteers of the microemulsion β-carotene preparation as described in Example 1.2 with a conventional dispersion preparation prepared using a β carotene water dispersible powder (tradename BETATENE, 2.5%. available from Henkel Ireland Ltd. Cork, Ireland). The preparations were drinks containing 15 mg of β carotene in 250 mls (as in Example 1.2). A placebo was included that looked and tasted the same as the other two products but contained no β carotene.

Recipes for the three variants used in the comparative bioavailability study

| Ingredient | Placebo (g/l) | Microemulsion drink preparation (g/l) | Dispersion drink preparation (g/l) |
| --- | --- | --- | --- |
| glucose syrup | 239.42 | 239.42 | 239.42 |
| flavourings | 0.12 | 0.12 | 0.12 |
| sodium benzoate | 0.28 | 0.28 | 0.28 |
| ascorbic acid | 0.25 | 0.25 | 0.25 |
| lactic acid | 0.97 | 0.97 | 0.97 |
| citric acid | 1.75 | 1.75 | 1.75 |
| caffeine | 0.09 | 0.09 | 0.09 |
| sunset yellow | 0.056 | — | — |
| β carotene as microemulsion | — | 0.06 | — |
| β carotene as dispersion | — | — | 0.06 |
| water to volume |  |  |  |

Specification for the Three Products
Brix 18.0±0.2°
Acidity 0.29±0.03% W/W (expressed as citric acid monohydrate)

Subjects received a single 250 ml serving of either the placebo or the microemulsion drink or the dispersion drink according to a Latin square randomisation schedule.

Blood samples were initially collected weekly for three weeks pre-dose and then at appropriate times for 11 days post-dose. Serum was analysed for β-carotene using a fully validated HPLC method. The treatment periods were separated by nine days.

Figure 5:
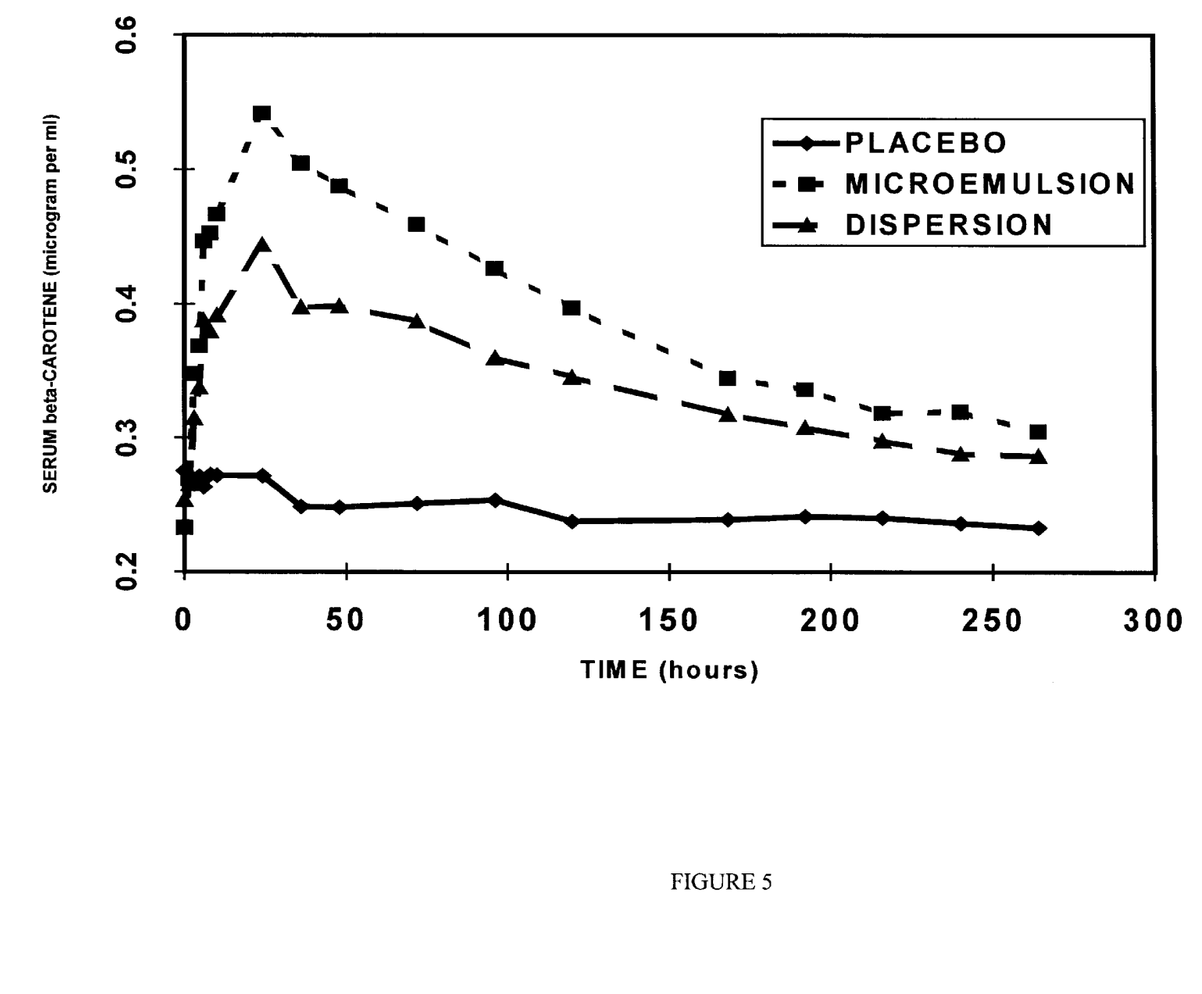
FIG. 5: Beta-carotene serum concentration for 11 days post dose.

FIG. 5 shows the β-carotene serum concentration for the 11 days post dose for the two test preparations and placebo.

The microemulsion and dispersion preparations were found to be different in both the mean maximum serum beta-carotene concentration and the areas under the curves. Both these differences were significant at the 0.1% level. From this it is concluded that β-carotene is significantly more bioavailable when administered as a microemulsion compared to a conventional dispersion.

What is claimed is:

1. A method for enhancing the stability of an optically clear syrup formulation containing an oil-soluble ingredient, wherein an aqueous composition is formed by
   i) mixing 0.1–2.0% w/w of the oil-soluble ingredient as a 20 to 30% w/w dispersion in a consumable or essential oil with 2 to 10% w/w of an emulsifier mixture having an HLB (hydrophilic lipophylic balance) value between 10 and 18, and
   wherein the emulsifier mixture is a combination of a primary surfactant and a secondary or cosurfactant, and the fatty acid profile of the emulsifier mixture matches the fatty acid profile of the dispersion of the oil-soluble ingredient, and the HLB value of the primary surfactant is greater than that of the cosurfactant; and the weight ratio of the dispersion of the oil-soluble ingredient to emulsifier mixture is between 1:1 and 1:7, and the ratio of primary to cosurfactant is between 10:1 and 200:1; and
   ii) forming a transparent mixture by heating to between 25 and 150° C.; and
   iii) combining the transparent mixture with water while continuously stirring; and
   iv) adding said aqueous composition to a syrup concentrate.

2. A method according to claim 1 wherein in the emulsion mixture is added to the water.

3. A method according to claim 1 wherein one or more antioxidants is first dispersed in the emulsifier mixture.

4. An optically clear syrup formulation obtained according to the method of claim 1.

5. A formulation according to claim 4 wherein the ratio of primary to cosurfactant is between 20:1 and 50:1.

6. A formulation according to claim 5 wherein the ratio of primary to cosurfactant is about 30:1.

7. A formulation according to claim 4 wherein the amount of oil soluble ingredient is 0.1–1.0%.

8. A formulation according to claim 4 wherein the amount of emulsifier is less than 6%.

9. A formulation according to claim 4 which further comprises an antioxidant.

10. A formulation according to claim 9 wherein the antioxidant is present in the amount of 0.3–0.5%.

11. A formulation according to claim 10 which the antioxidant is ascorbic acid or alpha-tocopherol or a mixture thereof.

12. A process for enhancing the stability of an optically clear syrup formulation containing a biologically active oil, wherein an aqueous composition is formed by
   i) mixing 0.001–2.0% w/w of the biologically-active oil with 2–10% w/w of an emulsifier mixture having an HLB (hydrophilic lipophylic balance) value between 10 and 18, and wherein the emulsifier mixture is a combination of a primary surfactant and a secondary or cosurfactant, wherein the fatty acid profile of the emulsifier mixture matches the fatty acid profile of the biologically-active oil, the HLB value of the primary surfactant is greater than that of the cosurfactant, the weight ratio of the biologically-active oil to emulsifier mixture is between 1:1 and 1:7 and the ratio of primary to cosurfactant is between 10:1 and 200:1;

ii) forming a transparent mixture by heating to between 25 and 150° C.; and iii) combining the transparent mixture with water while continuously stirring; and iv) adding said aqueous composition to a syrup concentrate.

13. An optically clear syrup formulation obtained according to the method of claim 12.

14. The formulation according to claim 13 which further comprises one or more antioxidants.

15. The formulation according to claim 14 in which the antioxidant is ascorbic acid or alpha-tocopherol or a mixture thereof.

16. The formulation according to claim 14 wherein one or more antioxidants are first dispersed in the emulsifier mixture.

17. The formulation according to claim 13 wherein the ratio of primary surfactant to cosurfactant is between 20:1 and 50:1.

18. The formulation according to claim 17 wherein the ratio of primary surfactant to cosurfactant is about 30:1.

19. The process according to claim 12 wherein in the emulsion mixture is added to the water.

* * * * *